United States Patent [19]

Simpson et al.

[11] Patent Number: 5,122,141
[45] Date of Patent: Jun. 16, 1992

[54] MODULAR INTRAMEDULLARY NAIL

[75] Inventors: George E. Simpson, Fort Wayne; John D. Miser, Warsaw; Mark A. Bryant, Auburn, all of Ind.

[73] Assignee: Zimmer, Inc., Warsaw, Ind.

[21] Appl. No.: 575,267

[22] Filed: Aug. 30, 1990

[51] Int. Cl.⁵ ................................. A61F 2/28
[52] U.S. Cl. ........................ 606/62; 606/63; 606/64
[58] Field of Search ............ 606/53, 60, 62, 63, 606/64, 65, 66, 72, 73

[56] References Cited

U.S. PATENT DOCUMENTS

| | | | |
|---|---|---|---|
| 3,846,846 | 11/1974 | Fischer | 606/72 X |
| 4,622,959 | 11/1986 | Marcus | 606/64 |
| 4,776,330 | 11/1988 | Chapman et al. | 606/64 |
| 4,805,607 | 2/1989 | Engelhardt et al. | 606/64 X |
| 4,858,601 | 8/1989 | Glisson | 606/65 X |
| 4,875,475 | 10/1989 | Comte et al. | 606/64 X |
| 4,940,467 | 7/1990 | Tronzo | 606/65 X |

FOREIGN PATENT DOCUMENTS 1031128  6/1953  France ...................... 606/63

Primary Examiner—Robert A. Hafer
Assistant Examiner—Sam Rimell
Attorney, Agent, or Firm—Gene Warzecha

[57] ABSTRACT

An intramedullary nail system and method for providing the capability of creating intramedullary nails of any desired length by a combination of a small number of base nail members adapted to be joined to any one of a variety of hollow extension nail members. Any selected extension nail member may be axially connected to any selected base nail member in order to prevent axial separation of the members. Additionally, each extension nail member is provided with transverse openings adapted to receive a bone screw to secure the intramedullary nail within the bone to be repaird. The extension nail member is infinitely rotationally adjustable about the axis of the base nail member in order to enable the fixation of the extension member with any desired degree of anteversion prior to final assembly of the base nail member with the extension nail member.

10 Claims, 3 Drawing Sheets

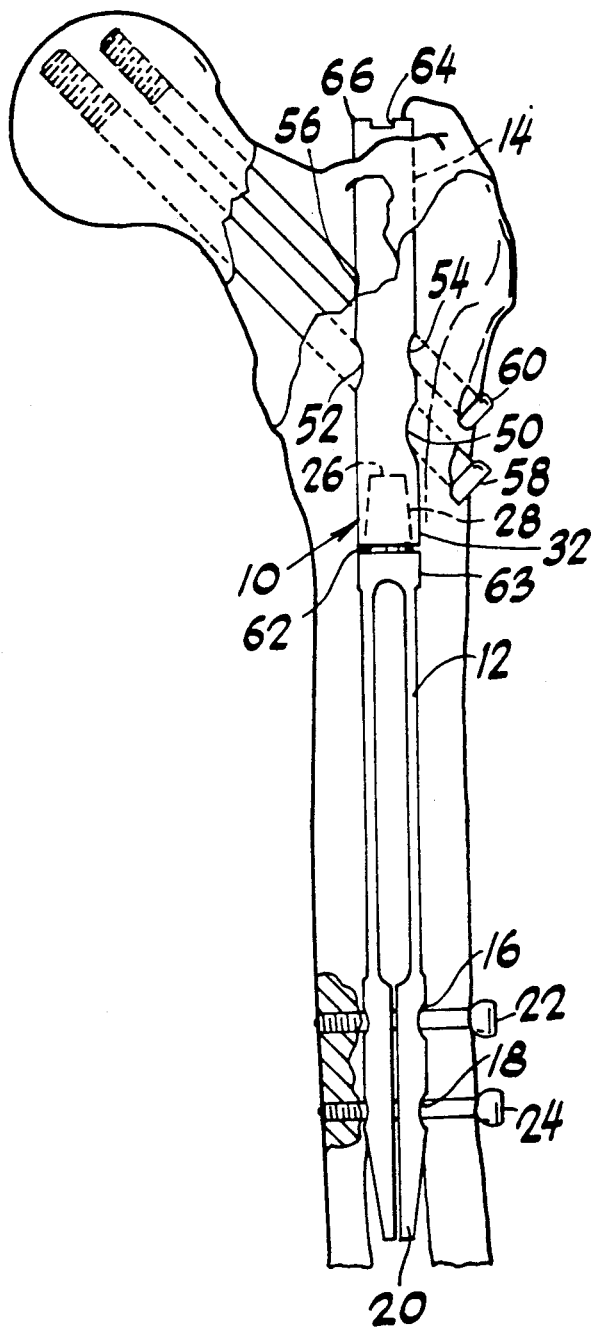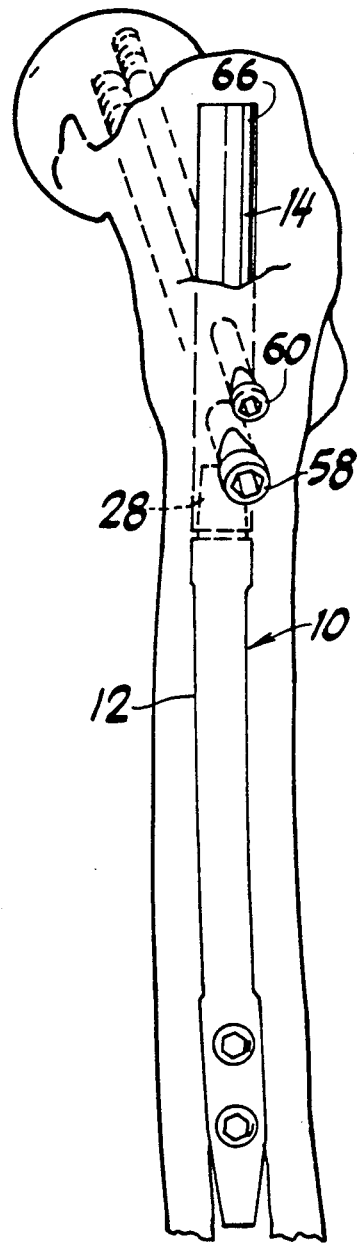
FIG. 1
FIG. 2

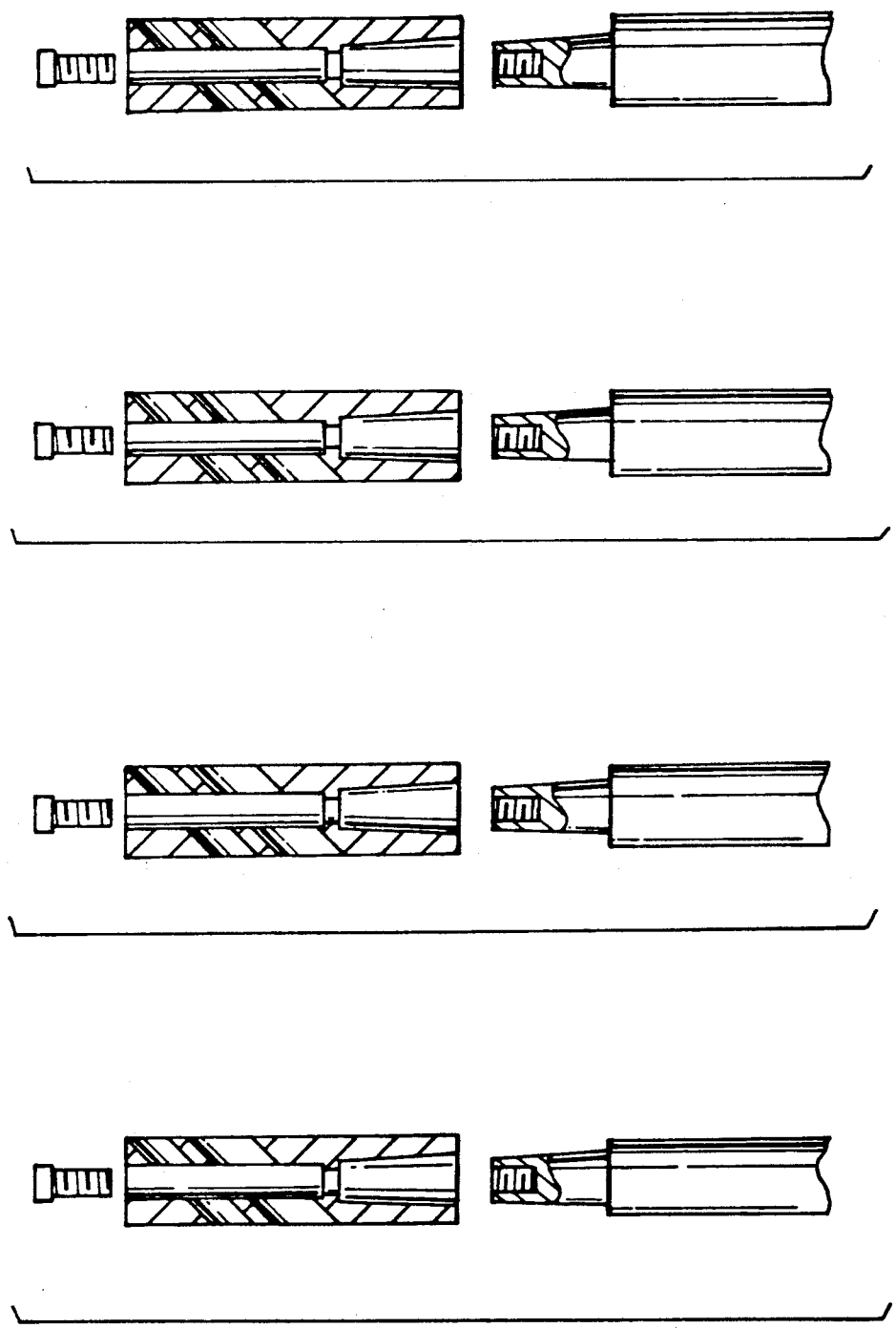

MODULAR INTRAMEDULLARY NAIL

BACKGROUND OF THE INVENTION

1. Field of the Invention

The invention relates generally to internal fracture fixation devices and, in particular, to intramedullary nail systems for the internal fracture fixation of long bones.

2. Description of the Prior Art

Intramedullary nails have long been used for internal fracture fixation. Generally, such a device comprises an extended hollow shaft having a predetermined cross-section and provided with transverse apertures at selected locations along its length. The nail is inserted into an intramedullary canal of a long bone and secured within the bone by transverse bone screws placed through aligned apertures in the nail.

Because the length of the intramedullary nail must be matched to the length of the bone to be repaired, prior art intramedullary nails are produced in a variety of lengths and diameters. In order to limit the number of sizes which must be carried in inventory, recent intramedullary nails have been produced as modular systems having a limited number of base nail members provided in a uniform length and a much larger variety of extension members in varying lengths and diameters. A selected extension member can be joined to any selected base nail member to produce an intramedullary nail of any desired length.

An additional consideration with intramedullary nails is that they must be transversely secured within the bone as mentioned above. Some bone screws are usually inserted in the proximal and distal ends of the nail, the former being often tilted to engage the femoral head with a certain degree of anteversion. Because the intramedullary nails generally have a cross-section which prevents their rotation within the intramedullary canal, the nail must be inserted into the canal with the proximal transverse openings generally aligned with the proper degree of anteversion in order to enable the transverse bone screws to be received within the femoral head. With respect to unitary intramedullary nails (as opposed to the aforementioned modular intramedullary nails), such as, for example, the unitary intramedullary nail shown in U.S. Pat. No. 4,622,959 (Marcus), once the nail is inserted into the canal, it cannot be rotated and, therefore, rotational positioning is somewhat critical prior to insertion of the nail into the canal. While modular intramedullary nail systems do not have quite the same limitation in anteversion adjustment of the proximal bone screw, as noted below known modular systems are limited in the available degree of anteversion adjustment.

One type of modular intramedullary nail system has been disclosed in U.S. Pat. No. 4,805,607 (Engelhardt et al.). The intramedullary nail of Engelhardt is provided with an extension member available in different lengths and diameters. While the Engelhardt device is advantageous in providing a femoral intramedullary system capable of being adapted to a variety of different length bones, it is incapable of infinite anteversion adjustment of the extension member relative to the base nail. The Engelhardt intramedullary nail secures the extension member to the end of the base nail by means of a pair of resilient tongs on the base member passing through a narrowed aperture on the extension member so that, upon engagement of the two members, axial separation is prevented although the extension member may still rotate relative to the base member. This rotation is necessary because, while the base member of the Engelhardt device does not require precise rotational positioning within the femur, the device does require a transverse screw to be threadably engaged through the extension member and between the tongs on the base member to secure the angular orientation of the extension member base member relative to the base member and to prevent the tongs from accidentally coming together and enabling axial separation of the extension from the base member. However, the Engelhardt arrangement enables the extension member to be secured in only one of two orientations relative to the tongs because the transverse locking screw must pass between the tongs. Consequently, the Engelhardt device is incapable of being easily implanted with the numerous degrees of anteversion which may be encountered by an orthopedic surgeon in various patients It is an object of this invention to provide a modular intramedullary nail system having a plurality of base nail members suitable for use with a plurality of extension nail members of varying length and/or diameter.

It is an additional object of this invention to provide a modular intramedullary nail capable of rotatably receiving a variety of extension members of selected length, the extension members capable of being secured in any desired angular orientation relative to the base portion of the intramedullary nail while also adapted to be axially secured to prevent axial separation of the two components.

SUMMARY OF THE INVENTION

These and other objects of the invention are achieved by the preferred embodiment disclosed herein which is a modular intramedullary nail comprising an elongated base portion adapted to be non-rotatably embedded in a bone, the base portion having a leading end and a trailing end. A hollow cylindrical extension portion is selected from a variety of sizes, each size adapted to be axially aligned with the base portion and is initially rotatably secured to the trailing end thereof. The extension portion has at least one pair of opposed transverse throughbores extending therethrough. A conical male portion is integrally formed in the trailing end of the base portion and an axially aligned threaded bore is formed in the end of the conical male portion. A complementarily shaped conical female portion is integrally formed in the leading end of the extension member. Joining the male and female conical portions enables the extension member to be rotationally positioned on the base member. A radially inwardly extending flange situated adjacent the apex of the conical female portion is adapted to be adjacent to, but not necessarily touch the trailing end of the conical male portion, the flange being situated between the pair of transverse throughbores and the base portion. A screw is threadably received within the bore of the male conical portion and secures the flange to prevent axial separation of the two components.

The invention also includes the method for implanting the aforementioned intramedullary nail, the method comprising the steps of implanting an elongated base nail member within the intramedullary canal of a long bone; providing the trailing end of the base nail member with a tapered locking surface and an axially aligned threaded bore; axially aligning with the trailing end of said the nail member an extension nail member having a radially inwardly extending flange and having at least one pair of transversely aligned openings, each pair for receiving therethrough a bone screw adapted to secure the extension nail member; loosely axially securing said extension nail member to the base nail member by engaging a locking screw in the axially aligned threaded bore of the base nail member; rotating the extension member axially to align at least one pair of the transversely aligned openings with a desired degree of anteversion; tightening the axial screw to prevent axial separation of the extension nail member from the base nail member; inserting a bone screw through at least one pair of the transversely aligned openings and into the adjacent bone in order to secure the extension member within the bone.

BRIEF DESCRIPTION OF THE DRAWINGS

FIG. 1 is a diagrammatic front elevational view of a preferred embodiment of the invention implanted within a human femur.

FIG. 2 is a right side elevational view of FIG. 1.

FIGS. 4a, 4b, 4c and 4d are exploded views of several portions of another embodiment of the invention shown in FIGS. 1 and 2.

DESCRIPTION OF THE PREFERRED EMBODIMENT

Figure 3C:
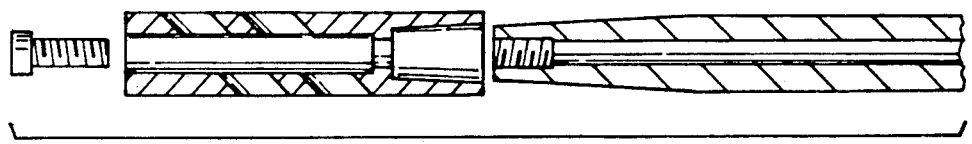
FIGS. 3a, 3b and 3c are exploded views of several portions of another embodiment of the invention shown in FIGS. 1 and 2.

As shown in the drawings, intramedullary nail 10 comprises a base nail member 12 and an extension nail member 14 adapted to be matingly connected to base nail member 12 to produce an intramedullary nail of a particular length selected by the surgeon.

Base nail member 12 may have any desired cross-sectional shape and is provided with a pair of transverse bores 16 and 18 adjacent its distal tip 20, the bores adapted to receive bone screws 22 and 24 in order to secure the distal end of the base nail member within the intramedullary canal. The proximal end 26 of base nail member 12 is provided with a conical tapered extension 28. In the preferred embodiment, the conical portions have what is commonly termed a "Morse" taper which will be understood by those skilled in the art to define a conical surface the slope of which is within a predetermined range of angularity relative to the axis of the nail member. Other taper profiles may also be suitable.

Conical extension 28 is shaped to be mateably received within conical bore 30 formed into the distal end 32 of cylindrical extension member 14. The innermost end of conical bore 30 is provided with a radially inwardly extending flange 34 having a central aperture 36 and adapted to overlie proximal end 38 of base nail member 12. The term "overlie" as used herein is intended to mean that the flange has some portion of its surface situated above the flat surface of proximal end 38. The term may include abutting contact of flange 34 and end 38 as well as some spaced relationship therebetween. The proximal end 38 is provided with an axially aligned threaded bore 40 adapted to be engaged by threaded screw 42, the head 44 of which is sized to fit within channel 46 of the extension member while being large enough to press flange 34 against end 38. Threaded bore 40 may be threaded immediately adjacent end 38 or the threads may start at some predetermined point below that surface. Additionally, while not shown it should be understood that threaded bore 40 may extend into the body of nail member 12 below the taper.

Extension member 14 is provided with a pair of transversely aligned, diametrically opposed openings 50, 52 and 54, 56. As best seen in FIGS. 1 and 2, openings 50 and 52 are intended to receive bone screw 58 and openings 54 and 56 are intended to receive bone screw 60. Transverse openings 50, 52 and 54, 56 may be inclined with respect to the vertical as best seen in FIG. 2 and may be of identical size as shown in FIG. 3. Alternately, one pair of openings may be smaller than the other to receive a bone screw of a smaller diameter.

Figure 3B:
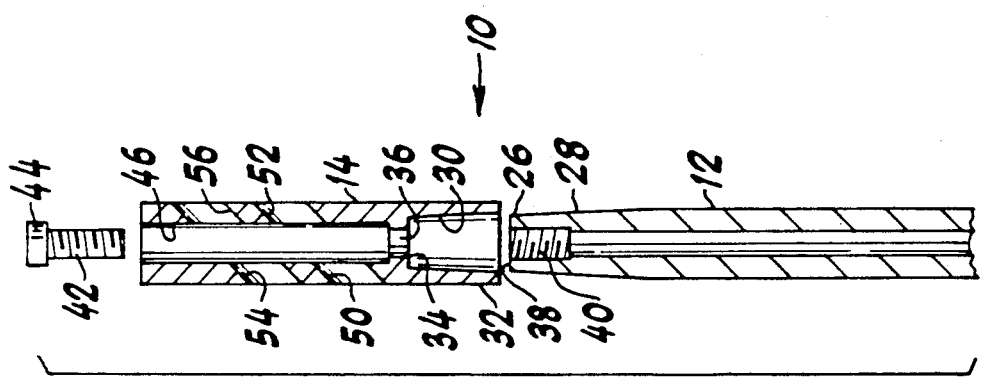
Figure 3A:
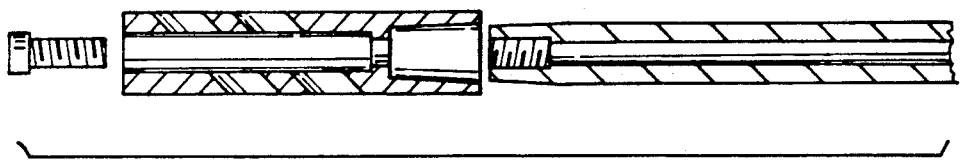

As shown in FIGS. 1 and 2, the bottom end of conical extension 28 may terminate in an annular shoulder 62, the existence and size of which depends upon the relative size of the diameter of conical end 28 and the outside diameter of the extension member 14. The invention enables the joinder of a variety of extension nail member sizes with a variety of base nail member sizes all of which are provided with the same size tapered connection. With any given size diameter of conical section 28 and corresponding bore 30, the outer diameters of cylindrical extension member 14 and the cylindrical proximal portion 63 of base nail member 12 may be made identical merely by adjusting the width of shoulder 62. It should be understood, however, that the outer diameter of extension member 14 need not necessarily be equal to the outer diameter of base nail member 12. While gross differences between the two diameters may be undesirable, a certain minor range of different diameters is acceptable. For example, as shown in FIGS. 3a, 3b and 3c an extension nail member having a 13 mm diameter is usable with a base nail member having a diameter of 10 mm, 11 mm and 12 mm, respectively, all with the same degree of Morse taper. Also, as best seen in FIGS. 4a, 4b, 4c and 4d, and 18 mm diameter extension nail member is usable with a base nail member having a diameter of 15 mm, 16 mm, 17 mm and 18 mm, respectively, also with the same degree of Morse taper as the aforementioned 13 mm example. As clearly seen by comparing the views of FIGS. 3 and 4, depending upon the difference in diameters between the extension member and the base nail member, there may or may not be a shoulder 62 present in any particular combination of members 12 and 14.

Referring now to FIGS. 1 and 2, the ability of the preferred embodiment of the invention to be assembled with an infinite degree of anteversion adjustment is illustrated. In a normal procedure for implanting intramedullary nail 10, a surgeon would select a certain length base nail member 12 and implant it into the intramedullary canal in a relatively conventional manner with the conventional degree of care to align distal apertures 16 and 18 as desired. Depending upon the length of the bone and the depth to which member 12 was inserted, the surgeon would then select a certain size extension member 14. The latter would be inserted into the intramedullary canal in order to have its distal end placed adjacent to the proximal end of the already implanted base nail member. While the surgeon may generally align the transverse openings of the extension member with the proper degree of anteversion, no extraordinary effort is required to make this alignment because even after the cylindrical extension nail member is inserted into the intramedullary canal, and before it is firmly joined to the base nail member 12, extension nail member 14 may be rotated with, for example, an appropriate tool inserted into a slot such as 64 formed in the proximal end 66 of the extension member in order to align its transverse openings with the precise degree of anteversion required. Since there may be instances where the surgeon will not be able to see the actual transverse openings, a specific orientation is provided between the alignment of the transverse openings and the alignment of transverse slot 64. Obviously, fluoroscopic examination may be used to confirm alignment. Once the surgeon has selected the required degree of anteversion, extension member 14 may be tapped into place on conical member 28 in order to firmly lock the two components rotationally and, because of the taper, even axially. To insure that the components do not become axially separated, screw 42 is then inserted into the channel 46 of the extension member and threaded into bore 40. Finally, bone screws 58 and/or 60 are transversely inserted (with the aid of fluoroscope, if desired) in order to firmly secure the entire intramedullary nail assembly into the patient. The bone screws also prevent screw 42 from accidentally loosening and migrating into the body of the patient.

In order to more rigidly secure the base nail and the extension member, the transverse openings are used in a retrograde fashion as shown in FIG. 2. If desired, however, it should be clear to those skilled in the art that the extension member only needs to be rotated 180° in order to enable an antegrade fixation of the transverse locking screws.

It will be understood by those skilled in the art that numerous other modifications and improvements may be made to the preferred embodiment of the invention disclosed herein without departing from the spirit and scope thereof.

What is claimed is:

1. A modular intramedullary nail comprising:
   an elongated base portion adapted to be non-rotatably embedded in a bone, said base portion having a distal end and a proximal end;
   a hollow cylindrical extension portion adapted to be axially aligned with said base portion and initially rotatably secured to the proximal end thereof, said extension portion having at least one pair of opposed transverse throughbores extending therethrough;
   means for rotatably interconnecting said base portion and said extension portion, said means comprising:
   a conical male portion and an axially aligned threaded bore formed in the proximal end of said base portion;
   a conical female portion formed in the distal end of said extension member, said female portion shaped complementarily to said male portion;
   a radially inwardly extending flange situated adjacent the apex of said conical female portion and adapted to overlie the proximal end of said conical male portion, said flange being situated between said at least one pair of transverse throughbores and said base portion; and
   a screw for being threadably received within said bore of said male conical portion and for securing said flange thereto.

2. A modular intramedullary nail according to claim wherein said at least one pair of opposed transverse throughbores is oblique to the axis of said extension portion.

3. A modular intramedullary nail comprising:
   a base nail member;
   a hollow cylindrical extension member for being secured to one end of said base nail member in axial alignment therewith, said extension member provided with at least one pair of openings therethrough said openings being aligned along a line inclined relative to an axis of said extension member;
   means for axially securing said extension member to said base nail member while enabling unrestricted rotation of said extension member relative to said base nail member so as to enable infinite anteversion alignment of said at least one pair of transversely aligned openings relative to the axis of said base nail member; and
   means engageable with said at least one pair of transversely aligned openings for securing said extension member in a desired rotational position relative to the axis of said base nail member.

4. A modular intramedullary nail according to claim 3 wherein said extension member and said base nail member are provided with mutually engaging tapered surfaces and wherein said axially securing means is a screw securing said extension member to a threaded bore in the end of said base nail member.

5. A modular intramedullary nail according to claim 4 wherein said rotatably securing means comprises a shaft member passing through said transversely aligned openings of said extension member proximally to said screw.

6. A modular intramedullary nail system comprising:
   a set of base nail members comprising a plurality of base nail members in a range of predetermined lengths and diameters, each base nail member having an axially aligned, conical male surface adjacent its trailing end, each of said conical male surfaces having an axial threaded bore and being of a uniform size throughout said range of base nail lengths and diameters;
   a set of extension members comprising a plurality of cylindrical extension members in a range of predetermined lengths and diameters, each extension member having a conical female bore adjacent its leading end and a radially inwardly extending flange adjacent the apex of said conical female bore, the female conical bores of each of said extension members being uniformly sized across the range of said extension members and complementarily shaped to mate with any one of said conical male surfaces each of said extension members being hollow and provided with at least one pair of transversely aligned openings in the cylindrical wall thereof for receiving a lag screw therethrough;
   a locking screw for threadably securing a selected one of said extension member to said base nail member.

7. A method for implanting an intramedullary nail into a bone comprising the steps of:
   implanting an elongated base nail member within the intramedullary canal of a long bone;
   providing the proximal end of said base nail member with a male tapered locking surface;
   axially aligning with the proximal end of said base nail member a hollow cylindrical extension nail member having a radially inwardly extending flange at the inner end of a female tapered locking surface formed in the distal end of said extension, said extension member having at least one pair of transversely aligned openings, each pair for receiving therethrough a bone screw adapted to secure said extension nail member within said bone;

connecting said extension nail member to said base nail member;

rotating the extension member to align at least one pair of said transversely aligned openings with a desired degree of anteversion;

inserting a bone screw through at least one pair of said transversely aligned openings and into the adjacent bone in order to secure said extension member within the bone.

8. A method according to claim 7 further comprising the steps of:

providing said proximal end of said base nail member with an axially aligned threaded bore;

engaging a locking screw in the axially aligned threaded bore of said base nail member;

tightening said axial screw to prevent axial separation of said extension nail member from said base nail member.

9. A method according to claim 8 further comprising the step of urging said extension nail member toward said base nail member before the step of tightening said axial screw.

10. A modular intramedullary nail according to claim 3 wherein said means for axially securing said extension member further serves to simultaneously maintain the longitudinal position of said openings fixed relative to said one end of said base nail member.

* * * * *